(12) United States Patent
Deng et al.

(10) Patent No.: US 9,730,675 B2
(45) Date of Patent: Aug. 15, 2017

(54) ULTRASOUND IMAGING SYSTEM AND AN ULTRASOUND IMAGING METHOD

(71) Applicant: KONINKLIJKE PHILIPS N.V., Eindhoven (NL)

(72) Inventors: Yinhui Deng, Shanghai (CN); Xiaomin Li, Shanghai (CN); Xiaolin Gu, Shanghai (CN); Vijay Thakur Shamdasani, Kenmore, WA (US); Ying Wu, Shanghai (CN)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/113,510

(22) PCT Filed: Jan. 21, 2015

(86) PCT No.: PCT/EP2015/051039
§ 371 (c)(1),
(2) Date: Jul. 22, 2016

(87) PCT Pub. No.: WO2015/110436
PCT Pub. Date: Jul. 30, 2015

(65) Prior Publication Data
US 2017/0007208 A1    Jan. 12, 2017

(30) Foreign Application Priority Data

Jan. 27, 2014  (CN) .................. PCT/CN2014/071553
May 15, 2014  (EP) ..................................... 14168419

(51) Int. Cl.
*A61B 8/00*    (2006.01)
*A61B 8/08*    (2006.01)
*A61B 8/14*    (2006.01)

(52) U.S. Cl.
CPC ................ *A61B 8/523* (2013.01); *A61B 8/14* (2013.01); *A61B 8/145* (2013.01); *A61B 8/4488* (2013.01);
(Continued)

(58) Field of Classification Search
CPC ....... A61B 8/523; A61B 8/145; A61B 8/4488; A61B 8/54; A61B 8/465; A61B 8/466; A61B 8/469; A61B 8/4494
(Continued)

(56) References Cited

U.S. PATENT DOCUMENTS 5,967,987 A  * 10/1999  Sumanaweera .......... A61B 8/06
                                                       600/454
6,234,968 B1 *  5/2001  Sumanaweera .......... A61B 8/14
                                                       600/443
(Continued)

FOREIGN PATENT DOCUMENTS

CN         201316280 Y     9/2009
WO       2009044316 A1     4/2009
(Continued)

*Primary Examiner* — Sanjay Cattungal

(57) ABSTRACT

The present invention provides an ultrasound imaging system and an ultrasound imaging method for improving the imaging quality of the desired imaging plane in the volume of interest of a subject. According to the present invention, it is possible to directly scan the desired imaging plane by exploiting the capability of a 2D matrix ultrasound transducer and/or the flexibility of the position/orientation of the ultrasound probe. In some cases, the setting parameters of the transducer elements can be adjusted so that the ultrasound signal transmitted from the transducer elements is able to derive ultrasound echo data of the desired imaging plane without moving the probe. In other cases where the desired imaging plane cannot be directly scanned without changing the position/orientation of the ultrasound probe, the position/orientation of the ultrasound probe can be
(Continued)

adjusted by means of user interaction, namely by outputting the instruction for guiding the user to move the probe so as to enable direct scanning of the desired imaging plane. In this way, the image of the desired imaging plane is not reconstructed by interpolation of the ultrasound echo data of the plurality of scanning planes (which are determined by the setting parameters of the transducer elements), but instead it is reconstructed from the ultrasound echo data of the desired imaging plane itself. In other words, the desired imaging plane is directly scanned. Thus, the image quality of the desired imaging plane is improved and may help doctors conduct a more accurate diagnosis.

11 Claims, 3 Drawing Sheets

(52) U.S. Cl.
CPC ............ *A61B 8/4494* (2013.01); *A61B 8/465* (2013.01); *A61B 8/466* (2013.01); *A61B 8/469* (2013.01); *A61B 8/483* (2013.01); *A61B 8/54* (2013.01)

(58) Field of Classification Search
USPC .................................................. 600/437–469
See application file for complete search history.

(56) References Cited

U.S. PATENT DOCUMENTS

| | | | |
|---|---|---|---|
| 6,669,641 | B2 | 12/2003 | Poland et al. |
| 6,755,786 | B2 | 6/2004 | Frisa et al. |
| 7,998,074 | B2 * | 8/2011 | Chomas .................. A61B 8/14 600/437 |
| 8,073,215 | B2 | 12/2011 | Lu et al. |
| 2003/0097068 | A1 * | 5/2003 | Hossack .............. A61B 8/5276 600/443 |
| 2007/0088213 | A1 | 4/2007 | Poland |
| 2009/0149757 | A1 | 6/2009 | Liu et al. |
| 2009/0221908 | A1 | 9/2009 | Glossop |
| 2010/0260398 | A1 | 10/2010 | Ma et al. |
| 2012/0150039 | A1 | 6/2012 | Liu et al. |
| 2012/0157845 | A1 | 6/2012 | Rabben et al. |
| 2013/0194890 | A1 | 8/2013 | Schauf |

FOREIGN PATENT DOCUMENTS

| | | |
|---|---|---|
| WO | 2010106379 A1 | 9/2010 |
| WO | 2011085469 A1 | 7/2011 |

* cited by examiner

ULTRASOUND IMAGING SYSTEM AND AN ULTRASOUND IMAGING METHOD

This application is the U.S. National Phase application under 35 U.S.C. §371 of International Application No. PCT/EP2015/051039, filed on Jan. 21, 2015, which claims the benefit of European Patent Application No. 14168419.1, filed May 15, 2014, and of International Application No. PCT/CN2014/071553, filed Jan. 27, 2014. These applications are hereby incorporated by reference herein.

FIELD OF THE INVENTION

The present invention relates to ultrasound imaging, more particularly to an ultrasound imaging system and an ultrasound imaging method for improving the imaging quality of the desired imaging plane in the volume of interest of a subject.

BACKGROUND OF THE INVENTION

A conventional one-dimensional (1D) ultrasound probe comprises a line of transducer elements from which ultrasonic signals may be emitted. Furthermore, an image plane underneath the transducer elements may be observed by detecting echoes of reflected ultrasonic signals coming from inhomogeneities of the observed region. By correctly positioning and moving the ultrasound transducer, a volume of interest of the subject comprising for example a lesion may be observed.

In ultrasound imaging of a volume of interest, a clinical challenge for doctors—especially junior doctors—is how to find an imaging plane for the volume of interest which is suitable or desirable for a certain clinical purpose. Supporting doctors to find the desired imaging plane is very valuable and highly required for clinical doctors. From the point of view of computerized techniques, the 2D image data acquired by the one-dimensional ultrasound probe may not provide sufficient information to do this, since the human body is a 3D object. Currently, the research work done for this goal is mainly based on 3D (acquired by using a matrix transducer comprising a two-dimensional array of transducer elements) or higher-dimensional data and once the high-dimensional data is obtained, the desired imaging plane with the object that doctors want to see may be determined and the corresponding 2D image of the desired imaging plane is displayed.

As regards the two-dimensional matrix ultrasound transducer, such a transducer may comprise an array of ultrasound transducer elements arranged in columns and rows. The transducer array face may still be rectangular as in the case of a one-dimensional ultrasound transducer, but the array of transducer elements is arranged in a two-dimensional matrix. This additional complexity may allow ultrasound beams to be steered and focused through a three-dimensional space rather than in only a plane. As is known to those skilled in the art, the two-dimensional matrix ultrasound transducer may acquire the three-dimensional volume data of the volume of interest from ultrasound echo data of a plurality of scanning planes in the volume of interest. The plurality of scanning planes may be determined by the setting parameters for the transducer elements, for example, which lines or rows are to be enabled, and the beam-forming parameters for the enabled elements.

Once the three-dimensional volume data of the volume of interest is acquired, any desired image plane can be reconstructed via computer processing algorithms, for example, by interpolation of the ultrasound echo data of the plurality of scanning planes.

Nevertheless, although it may be easier for doctors to find the desired imaging plane for the volume of interest with a two-dimensional matrix ultrasound transducer, the quality of the reconstructed and displayed 2D image of the desired imaging plane may be unsatisfactory.

Specifically, current automated means to reconstruct the 2D image of the desired imaging plane have some disadvantages, for example fixed enablement of the transmit elements of the matrix transducer regardless of the desirable imaging plane, etc. In other words, the image of the determined desired imaging plane may not be constructed in the transmit direction of the ultrasound signal. Since the ultrasound signal will have a signal focusing process and the corresponding interpolation process, if the image of the desired imaging plane is not generated in the transmit direction (i.e., not generated by the ultrasound echo data of the desired imaging plane itself) but reconstructed by interpolation of the ultrasound echo data of the plurality of scanning planes in the volume of interest, the quality of the constructed 2D image may be highly affected and sometimes clinical diagnosis cannot be performed for some applications where a high data quality is required.

SUMMARY OF THE INVENTION

Therefore, there is a need for a novel ultrasound imaging system and method, which is capable of improving the imaging quality of the desired imaging plane.

In accordance with an aspect of the present invention, there is proposed an ultrasound imaging system, comprising:

an ultrasound probe with a two-dimensional array of transducer elements, for transmitting ultrasound signals and acquiring three-dimensional volume data of a volume of interest of a subject when the probe is positioned at a first position on the subject and tilted at a first angle relative to the volume of interest and the transducer elements of the probe have a first set of setting parameters, wherein the three-dimensional volume data of the volume of interest comprises ultrasound echo data of a plurality of scanning planes defined by the first set of setting parameters;

a processing unit for determining a desired imaging plane for the volume of interest in accordance with the three-dimensional volume data and for determining a result whether there is a second set of setting parameters such that the ultrasound signal transmitted from the transducer elements having the second set of setting parameters is able to acquire ultrasound echo data of the desired imaging plane without moving the probe, wherein the processing unit is further configured to derive—if the result is YES—the second set of setting parameters, and to derive—if the result is NO—a second position, a second angle and a third set of setting parameters such that when the probe is moved to the second position on the subject and tilted at the second angle relative to the volume of interest, the ultrasound signal transmitted from the transducer elements having the third set of setting parameters is able to derive ultrasound echo data of the desired imaging plane;

a transducer controller for adjusting the transducer elements in accordance with the derived second set of setting parameters if the result is Yes, and adjusting the transducer elements in accordance with the derived third set of setting parameters if the result is NO; and a display for, if the result is NO, outputting an instruction to guide a user of the ultrasound imaging system to move the probe so as to be positioned at the second position and tilted at the second angle.

In this way, it is possible to directly scan the desired imaging plane by exploiting the capability of a 2D matrix ultrasound transducer and/or the flexibility of the position/orientation of the ultrasound probe. In some cases, the setting parameters of the transducer elements can be adjusted so that the ultrasound signal transmitted from the transducer elements is able to derive ultrasound echo data of the desired imaging plane without moving the probe. In other cases where the desired imaging plane cannot be directly scanned without changing the position/orientation of the ultrasound probe, the adjustment of the position/orientation of the ultrasound probe is possible by means of user interaction, namely outputting the instruction for guiding the user to move the probe so as to enable direct scanning of the desired imaging plane.

In this way, the image of the desired imaging plane is not reconstructed by interpolation of the ultrasound echo data of the plurality of scanning planes (which are determined by the setting parameters of the transducer elements), but the image is reconstructed from the ultrasound echo data of the desired imaging plane itself. In other words, the desired imaging plane is directly scanned. Thus, the image quality of the desired imaging plane is improved and may help doctors conduct a more accurate diagnosis.

In an embodiment of the present invention, the setting parameters of the transducer elements comprise which transducer elements are to be enabled and the beam-forming parameters for the enabled transducer elements.

As can be understood by those skilled in the art, the beam-forming parameters of the transducer elements may comprise, for example, the phase of the ultrasound signals transmitted by each of the enabled transducer elements and/or the beam-forming vectors adopted in the beam-forming element on the receiving side to synthesize the echo data of the ultrasound signals transmitted by the enabled transducer elements.

In an embodiment of the present invention, the elements of the transducer that should be enabled are determined first, and then the beam-forming parameters for the enabled elements are determined.

By first determining the corresponding elements of the transducer that should be enabled, it is possible to preliminarily constrain the set of planes that can be imaged in the volume of interest. Meanwhile, by not enabling all the elements the processing cost is reduced. Furthermore, the corresponding detailed direction of the transmitting signal is then determined by adjusting beam-forming parameters for the enabled elements. In this way, the transmitting signal from the enabled elements uniquely corresponds to the desired imaging plane.

In an embodiment of the present invention, the processing unit is configured to automatically determine the desired imaging plane for the volume of interest in accordance with the three-dimensional volume data, a clinical objective and a predetermined model.

By gaining prior-knowledge of the planes that doctors want to see, it is possible to have different options available if a predetermined model has been set for different clinical objectives. The plane detection methods could be different Hough transforms, segmentation-based methods or graphical models of different objects, etc. It should be noted that automatic determination of the desired imaging plane is realized in real-time here, which could provide more information for the whole of the process and for the following scanning plan as compared with conventional approaches.

In another embodiment of the present invention, the ultrasound imaging system may further comprise a user interface for receiving the user's input. In this case, the display may be further configured to display a plurality of images reconstructed from the three-dimensional volume data, and the processing unit may be further configured to determine the desired imaging plane for the volume of interest in accordance with the user's manual selection based on the plurality of images reconstructed from the three-dimensional volume data.

If the automatically determined imaging plane is not good enough or the automatic option is not available, doctors need to find the plane by themselves. Within the three-dimensional volume data, doctors manually move the plane and the plane position should be displayed in the current total 3D data. Since this should be performed in real-time during the scanning process, the interpretation of the displayed 2D image should not be more complicated than the conventional scanning operation. Meanwhile spatial information is provided, which makes it more convenient for doctors to interpret the image.

In accordance with another aspect of the present invention, there is proposed an ultrasound imaging method, comprising:

transmitting ultrasound signals and acquiring three-dimensional volume data of a volume of interest of a subject with an ultrasound probe having a two-dimensional array of transducer elements, wherein the probe is positioned at a first position on the subject and tilted at a first angle relative to the volume of interest and the transducer elements of the probe have a first set of setting parameters, and wherein the three-dimensional volume data of the volume of interest comprises ultrasound echo data of a plurality of scanning planes defined by the first set of setting parameters;

determining a desired imaging plane for the volume of interest in accordance with the three-dimensional volume data;

determining a result whether there is a second set of setting parameters such that the ultrasound signal transmitted from the transducer elements having the second set of setting parameters is able to acquire ultrasound echo data of the desired imaging plane without moving the probe;

deriving—if the result is YES:—the second set of setting parameters, and—if the result is NO:—deriving a second position, a second angle and a third set of setting parameters such that when the probe is moved to the second position on the subject and tilted at the second angle relative to the volume of interest, the ultrasound signal transmitted from the transducer elements having the third set of setting parameters is able to derive ultrasound echo data of the desired imaging plane; and adjusting the transducer elements in accordance with the derived second set of setting parameters if the result is Yes, and outputting an instruction to guide a user of the ultrasound imaging system to move the probe so as to be positioned at the second position and tilted at the second angle and adjusting the transducer elements in accordance with the derived third set of setting parameters if the result is NO.

As mentioned above, the ultrasound imaging method according to the present invention may improve the image quality of the desired imaging plane and may help doctors conduct a more accurate diagnosis since the image of the desired imaging plane is not reconstructed by processing the imaging data of one or more imaging planes different from the desired imaging plane but by directly processing the imaging data of the desired imaging plane.

Various aspects and features of the disclosure are described in further detail below. These and other aspects of the invention will be apparent from and elucidated with reference to the embodiment(s) described hereinafter.

DESCRIPTION OF THE DRAWINGS

The present invention will be described and explained hereinafter in more detail in combination with embodiments and with reference to the drawings, wherein.

Figure 1:
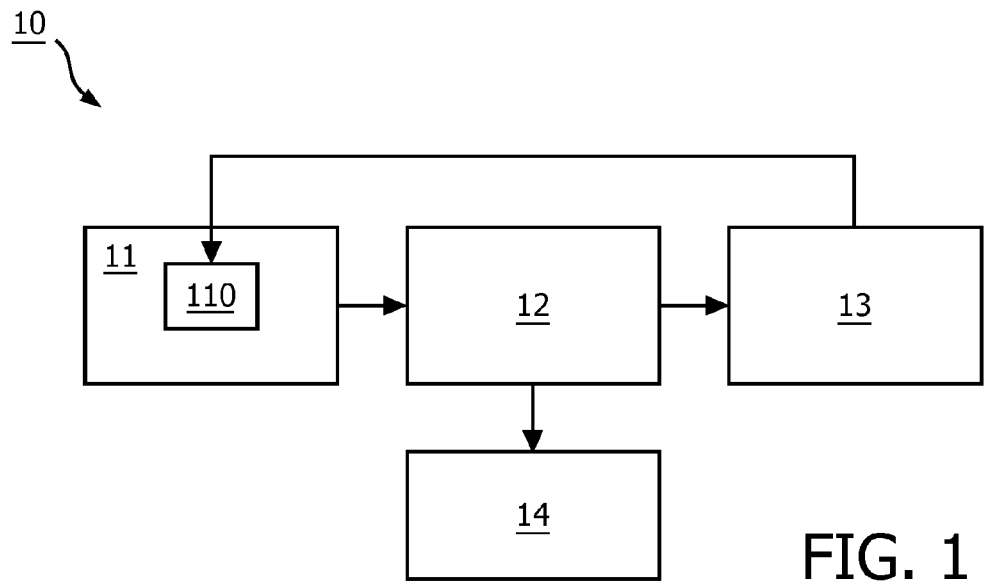
FIG. 1 is a block diagram of an ultrasound imaging system 10 according to the present invention.

The same reference signs in the figures indicate similar or corresponding features and/or functionalities.

DETAILED DESCRIPTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes.

FIG. 1 is a block diagram of an ultrasound imaging system 10 according to the present invention.

In the following, details of the ultrasound imaging system 10 will be described in conjunction with FIG. 2, which is a block diagram of the ultrasound imaging method 20 according to the present invention.

As can be seen from FIG. 1, the ultrasound imaging system 10 of the present invention comprises an ultrasound probe 11. According to the present invention, a two-dimensional array of transducer elements 110 is utilized in the probe 11, for transmitting ultrasound signals and acquiring three-dimensional volume data of a volume of interest of a subject (step 21 in FIG. 2). For example, the subject may be a patient and the volume of interest of the subject may be an organ of the patient.

In the following, the position at which the probe 11 is positioned on the subject when the three-dimensional volume data is acquired is referred to as the first position and the angle at which the probe is tilted relative to the volume of interest is referred to as the first angle.

Furthermore, as can be easily understood by those skilled in the art, a two-dimensional matrix ultrasound transducer may comprise an array of ultrasound transducer elements 110 arranged in columns and rows. The transducer array face may still be rectangular as in the case of a one-dimensional ultrasound transducer, but the array of transducer elements is arranged in a two-dimensional matrix. At the time of acquiring the three-dimensional volume data, a first set of setting parameters is predetermined for the transducer elements 110 of the probe 11. In other words, the first set of setting parameters determines which transducer elements are to be enabled as well as the beam-forming parameters for the enabled transducer elements. Therefore, the first set of setting parameters determines that a plurality of scanning planes of the two-dimensional matrix ultrasound transducer are arranged in columns or in rows, or even in diagonal directions. Accordingly, the acquired three-dimensional volume data of the volume of interest comprises ultrasound echo data of the plurality of scanning planes defined by the first set of setting parameters.

Figure 2:
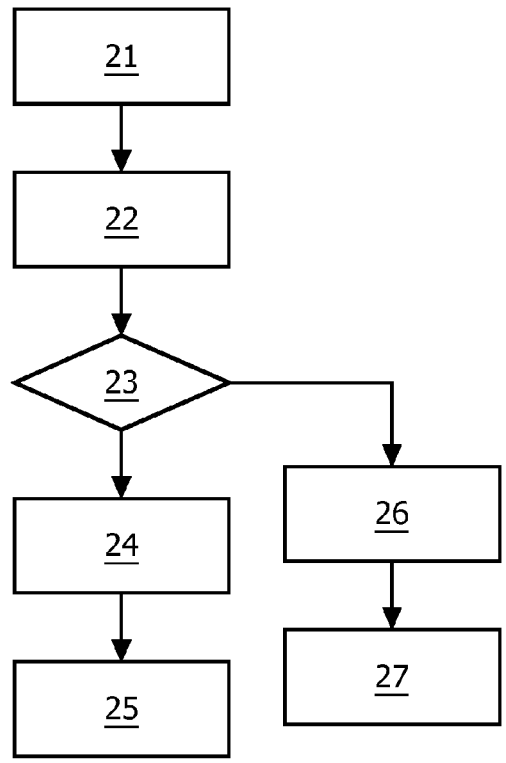
FIG. 2 is a block diagram of an ultrasound imaging method 20 according to the present invention.

As can be seen from FIG. 1, the ultrasound imaging system 10 according to an embodiment of the present invention further comprises a processing unit 12 for determining a desired imaging plane 1 for the volume of interest in accordance with the three-dimensional volume data (step 21 in FIG. 2).

In an embodiment of the present invention, the processing unit 12 may be configured to automatically determine the desired imaging plane 1 for the volume of interest in accordance with the acquired three-dimensional volume data, a clinical objective and a predetermined model.

By gaining prior-knowledge of the planes that doctors want to see, different options can be made available if a predetermined model has been set for different clinical objectives. The plane detection methods could be different Hough transforms, segmentation-based methods or graphical models of different objects, etc. It should be noted that the automatic determination of the desired imaging plane is realized in real-time here, which could provide more information for the whole of the process and for a following scanning plan as compared with conventional approaches.

In another embodiment of the present invention, the ultrasound imaging system 10 may further comprise a user interface for receiving the user's input. In this case, the display may be further configured to display a plurality of images reconstructed from the three-dimensional volume data, and the processing unit 12 may be further configured to determine the desired imaging plane 1 for the volume of interest in accordance with the user's manual selection based on the plurality of images reconstructed from the three-dimensional volume data.

If the automatically determined imaging plane is not good enough or the automatic option is not available, the ultrasound system can be further configured to allow doctors to find the plane by themselves. Within the three-dimensional volume data, doctors can be provided with means to manually move the plane, and the plane position should be displayed in the current total 3D data. Since this should be performed in real-time during the scanning process, the interpretation of the displayed 2D image should not be more complicated than the conventional scanning operation. Meanwhile the spatial information is provided, which makes it more convenient for doctors to interpret the image.

As can be easily understood by those skilled in the art, the desired imaging plane 1 for the volume of interest is determined by considering the particular anatomical structure of the volume of interest and the particular target in the volume of interest, for example a potential lesion, and therefore is usually not one of the scanning planes. However, only the image of the scanning plane is generated from the transmitting signal in the transmit direction. If the desired imaging plane 1 is not one of the scanning planes, the image thereof is not reconstructed in the transmit direction of the ultrasound signal, i.e., not generated by the ultrasound echo data of the desired imaging plane itself, but reconstructed by interpolation of the ultrasound echo data of the plurality of scanning planes in the volume of interest, but the quality of the reconstructed 2D image may be highly adversely affected and sometimes clinical diagnosis cannot be performed for applications where high data quality is required.

In view of the above, the present invention exploits the capability of a 2D matrix ultrasound transducer, in which the enabled transducer elements and the beam-forming parameters for the enabled elements may be adjusted so that the ultrasound signal transmitted from the enabled transducer elements is able to derive ultrasound echo data of the desired imaging plane without moving the probe or after moving the probe to another position and tilted at another angle relative to the volume of interest.

Accordingly, the processing unit 12 of the present invention is further used to determine a result whether there is a second set of setting parameters such that the ultrasound signal transmitted from the transducer elements having the second set of setting parameters is able to acquire ultrasound echo data of the desired imaging plane without moving the probe 11 (step 23 in FIG. 2).

If the result is YES, the processing unit 12 is further configured to derive the second set of setting parameters (step 24 in FIG. 2). In this case, a transducer controller 13 comprised in the ultrasound imaging system 10 then adjusts the transducer elements 110 in accordance with the derived second set of setting parameters (step 25 in FIG. 2).

However, if the result is NO, i.e., if the probe 11 has to be moved (i.e., either one of the first position and the first angle, or even both of the first position and the first angle have to be changed), the processing unit 12 is further configured to derive a second position and a second angle for the probe 11 and derive a third set of setting parameters for the transducer elements 110 such that when the probe 11 is moved to the second position on the subject and tilted at the second angle relative to the volume of interest, the ultrasound signal transmitted from the transducer elements having the third set of setting parameters is able to derive ultrasound echo data of the desired imaging plane (step 26 in FIG. 2). In this case, the transducer controller 13 then adjusts the transducer elements 110 in accordance with the derived third set of setting parameters (step 27 in FIG. 2).

In an embodiment of the present invention, the processing unit 12 performs steps 23, 24 and 26 based on the spatial positional relationship between the first position and the first angle of the probe and the desired imaging plane 1 and based on the layout of the transducer elements 110.

Figure 4A:
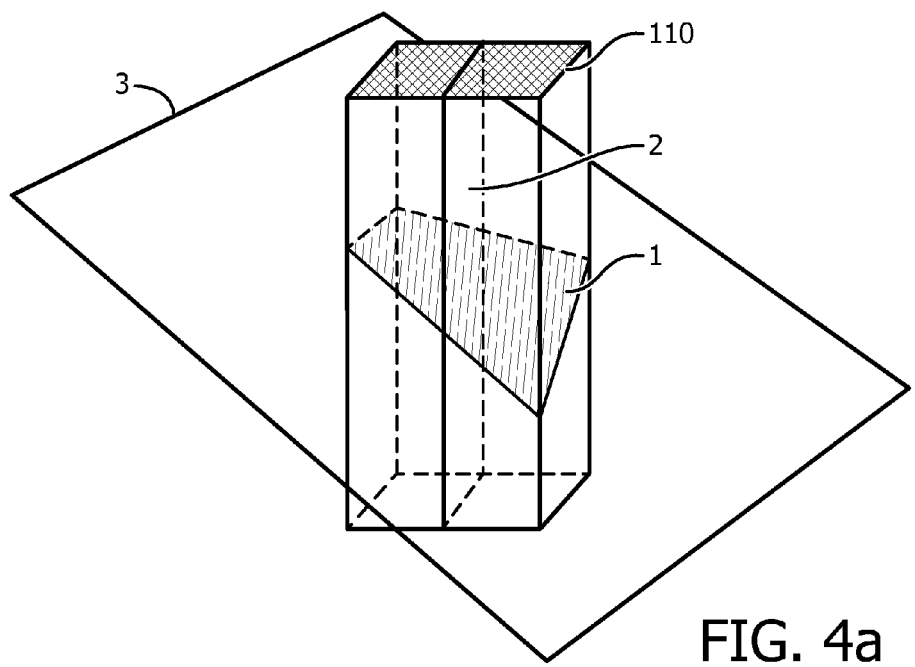
FIG. 4a and FIG. 4b illustrate, in the case of FIG. 3b, how the display of the ultrasound imaging system 10 outputs an instruction to guide a user of the ultrasound imaging system to move the probe according to an embodiment of the present invention.
Figure 4B:
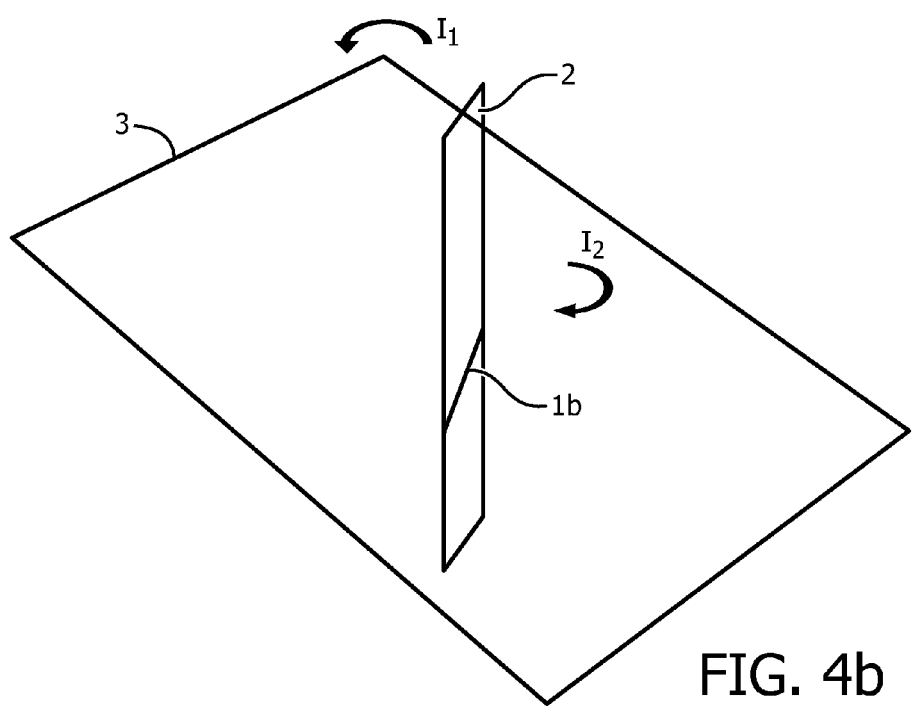

The ultrasound imaging system 10 according to an embodiment of the present invention further comprises a display 14. If the result is NO, i.e., if the probe 11 has to be moved, the display 14 is used to output an instruction to guide a user of the ultrasound imaging system 10 to move the probe 11 so as to be positioned at the second position and tilted at the second angle. The schematic view of how to guide the user to move the probe 11 is shown in FIG. 4a and FIG. 4b, and will be explained hereinafter.

In an embodiment of the present invention, the display 14 is further configured to display an image of the desired imaging plane 1, which is reconstructed from the ultrasound echo data of the desired imaging plane 1.

In this way, the image of the desired imaging plane 1 is not reconstructed by interpolation of the ultrasound echo data of the plurality of scanning planes (which correspond to the ultrasound signals transmitted from the initial enabled elements and initial beam-forming parameters), but reconstructed from the ultrasound echo data of the desired imaging plane itself. Thus, the image quality of the desired imaging plane 1 is improved and may help doctors conduct a more accurate diagnosis.

The details of step 23, i.e., the determination of whether there is a second set of setting parameters such that the ultrasound signal transmitted from the transducer elements having the second set of setting parameters is able to acquire ultrasound echo data of the desired imaging plane without moving the probe 11 is further elaborated hereinafter in conjunction with FIGS. 3a and 3b, which illustrate, respectively, a condition where the desired imaging plane 1 is intersected with the two-dimensional array of transducer elements 110, and a condition where the desired imaging plane 1 is not intersected with the two-dimensional array of transducer elements 110.

Figure 3A:
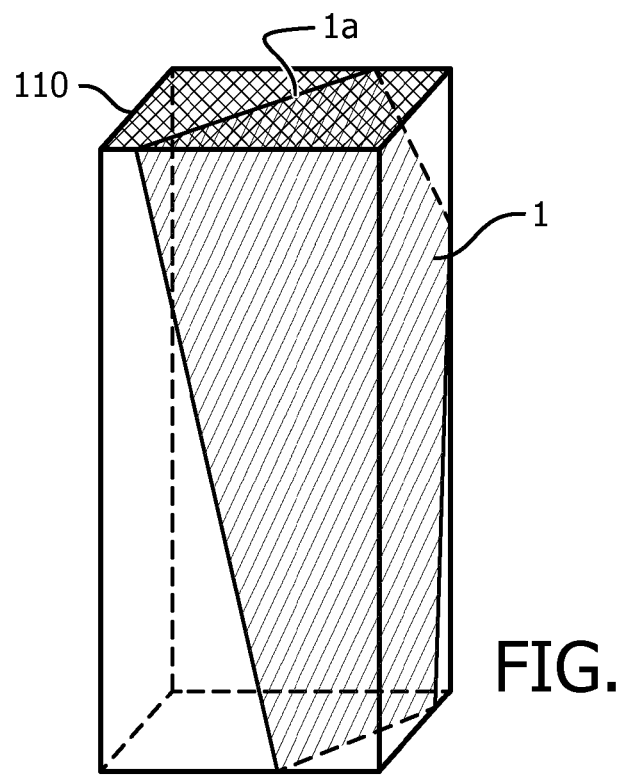
FIG. 3a illustrates a condition where the desired imaging plane is intersected with the two-dimensional array of transducer elements.

As can be understood from FIG. 3a, in the case that the desired imaging plane 1 is intersected with the two-dimensional array of transducer elements 110, it is determined that the result is YES, i.e., there is a second set of setting parameters such that the ultrasound signal transmitted from the transducer elements having the second set of setting parameters is able to acquire ultrasound echo data of the desired imaging plane without moving the probe 11.

Accordingly, the transducer elements on the intersection line 1a would be enabled and the transducer elements adjacent to the intersection line 1a would usually be enabled. This may preliminarily constrain the set of planes that can be imaged in the volume of interest.

Furthermore, the corresponding detailed direction of the transmitting signal is determined by adjusting beam-forming parameters for the enabled elements. In this way, the transmitting signal from the enabled elements uniquely corresponds to the desired imaging plane 1.

Figure 3B:
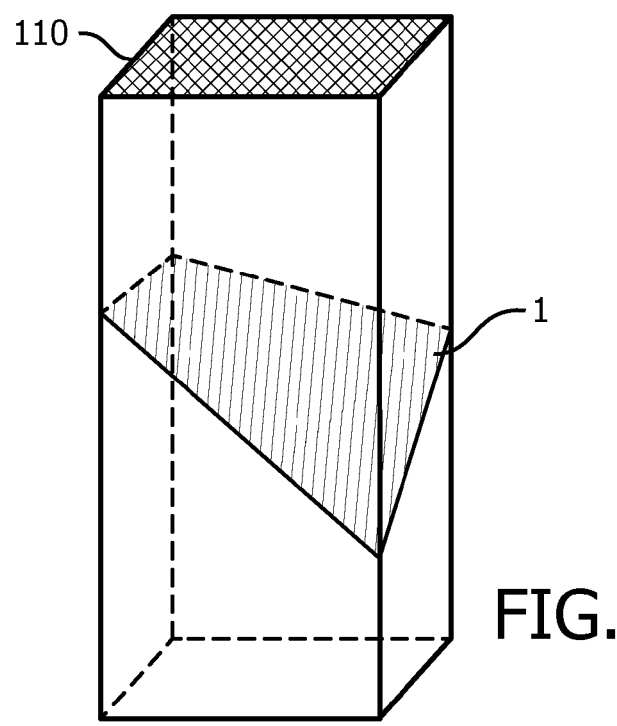
FIG. 3b illustrates a condition where the desired imaging plane is not intersected with the two-dimensional array of transducer elements.

As can be understood from FIG. 3b, in the case that the desired imaging plane 1 is not intersected with the two-dimensional array of transducer elements 110, it is determined that the result is NO, i.e., there is not a second set of setting parameters such that the ultrasound signal transmitted from the transducer elements having the second set of setting parameters is able to acquire ultrasound echo data of the desired imaging plane without moving the probe 11. In other words, according to the limited scale of the two-dimensional array of transducer elements 110, the desired imaging plane 1, which is not intersected with the two-dimensional array of transducer elements 110, cannot be imaged with a real transmitting signal of the elements without moving the probe to another position different from the first position.

As mentioned above, if the result is NO, i.e., if the probe 11 has to be moved, the processing unit 12 is further configured to derive a second position and a second angle for the probe 11 and derive a third set of setting parameters for the transducer elements 110 such that when the probe 11 is moved to the second position on the subject and tilted at the second angle relative to the volume of interest, the ultrasound signal transmitted from the transducer elements having the third set of setting parameters is able to derive ultrasound echo data of the desired imaging plane (step 26 in FIG. 2).

As can be easily understood by those skilled in the art, usually the second position and the second angle are both different from the first position and the first angle. However, in some cases, the second angle may be the same as the first angle.

FIG. 4a and FIG. 4b illustrate, in the case of FIG. 3b, how the display 14 of the ultrasound imaging system outputs an instruction to guide a user of the ultrasound imaging system to move the probe according to an embodiment of the present invention.

As mentioned above, in the case of FIG. 3b, the desired imaging plane 1 is not intersected with the two-dimensional array of transducer elements 110. As shown in FIGS. 4a and 4b, according to the layout of the transducer elements 110, a middle reference plane 2, which is underneath the centerline of the array of transducer elements 110, could be determined. Furthermore, according to the spatial positional relationship between the first position and the first angle of the probe 11 and the desired imaging plane 1, the second position, the second angle and the third set of setting parameters such that when the probe 11 is moved to the second position on the subject and tilted at the second angle relative to the volume of interest, the ultrasound signal transmitted from the transducer elements 110 having the third set of setting parameters is able to derive ultrasound echo data of the desired imaging plane 1.

For example, according to the spatial positional relationship between the middle reference plane 2 and the plane 3 in a 3D space containing the desired imaging plane 1, the processing unit 12 is able to calculate the second position that the probe 11 should be moved to. Further, according to the spatial positional relationship between the centerline of the array of transducer elements 110 and the intersection line 1b of the middle reference plane 2 with the desired imaging plane 1, the processing unit 12 is able to calculate the second angle at which the probe 11 should be tilted relative to the volume of interest. After that, the processing unit 12 may derive that, at the second position and the second angle, the transducer elements on the centerline of the array (and some elements adjacent to the centerline) should be enabled and the beam-forming parameters for the enabled transducer elements could be determined accordingly, so that the desired imaging plane 1 could be directly obtained by the transmitting signal from the enabled elements.

As can be understood by those skilled in the art, the above-mentioned middle reference plane 2 is only used as an embodiment; other reference planes may also be used and the second position, the second angle and the third set of setting parameters could be similarly derived according to the selection of the reference plane.

If the second position and the second angle have been derived, the display 14 of the ultrasound imaging system 10 then outputs an instruction to guide a user of the ultrasound imaging system 10 to move the probe 11, for example the moving direction indicated by I$_1$ in FIG. 4b to guide the user to move the probe 11 to the second position and the rotation direction indicated by I$_2$ in FIG. 4b to guide the user to achieve the second angle of the probe 11. The instruction can be output in a format of text, graphics, or a combination thereof. In some embodiments, the display 14 is capable of outputting audio, and the instruction can be output in an audio format.

Furthermore, as can be easily understood by those skilled in the art, in the apparatus claim enumerating several means, several of these means can be embodied by one and the same item of hardware. The mere fact that certain measures are recited in mutually different dependent claims does not indicate that a combination of these measures cannot be used to advantage.

It should be noted that the above-mentioned embodiments illustrate rather than limit the invention and that those skilled in the art would be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the system claims enumerating several units, several of these units can be embodied by one and the same item of software and/or hardware. The usage of the words first, second and third, et cetera, does not indicate any ordering. These words are to be interpreted as names.

The invention claimed is:

1. An ultrasound imaging system, comprising:
an ultrasound probe with a two-dimensional array of transducer elements, for transmitting ultrasound signals and acquiring three-dimensional volume data of a volume of interest of a subject when the probe is positioned at a first position on the subject and tilted at a first angle relative to the volume of interest and the transducer elements of the probe have a first set of setting parameters, wherein the three-dimensional volume data of the volume of interest comprises ultrasound echo data of a plurality of scanning planes defined by the first set of setting parameters;
a processing unit for determining a desired imaging plane for the volume of interest in accordance with the three-dimensional volume data and for determining a result whether there is a second set of setting parameters such that the ultrasound signal transmitted from the transducer elements having the second set of setting parameters is able to acquire ultrasound echo data of the desired imaging plane without moving the probe, wherein the processing unit is further configured—if the result is YES—to derive the second set of setting parameters; and—if the result is NO—to derive a second position, a second angle and a third set of setting parameters such that when the probe is moved to the second position on the subject and tilted at the second angle relative to the volume of interest, the ultrasound signal transmitted from the transducer elements having the third set of setting parameters is able to derive ultrasound echo data of the desired imaging plane;
a transducer controller for adjusting the transducer elements in accordance with the derived second set of setting parameters if the result is Yes, and for adjusting the transducer elements in accordance with the derived third set of setting parameters if the result is NO; and
a display for outputting—if the result is NO—an instruction to guide a user of the ultrasound imaging system to move the probe so as to be positioned at the second position and tilted at the second angle.

2. The ultrasound imaging system according to claim 1, wherein
the display is further configured to display an image of the desired imaging plane, which is reconstructed from the ultrasound echo data of the desired imaging plane.

3. The ultrasound imaging system according to claim 1, wherein
the setting parameters of the transducer elements comprise which transducer elements are to be enabled and the beam-forming parameters for the enabled transducer elements.

4. The ultrasound imaging system according to claim 1, wherein
the processing unit is configured to automatically determine the desired imaging plane for the volume of interest in accordance with the three-dimensional volume data, a clinical objective and a predetermined model.

5. The ultrasound imaging system according to claim 1, further comprising:
a user interface for receiving the user's input, wherein the display is further configured to display a plurality of images reconstructed from the three-dimensional volume data, and
wherein the processing unit is further configured to determine the desired imaging plane for the volume of interest in accordance with the user's manual selection based on the plurality of images reconstructed from the three-dimensional volume data.

6. The ultrasound imaging system according to claim 1, wherein
the processing unit determines a result whether there is a second set of setting parameters such that the ultrasound signal transmitted from the transducer elements having the second set of setting parameters is able to acquire ultrasound echo data of the desired imaging plane without moving the probe based on the spatial positional relationship between the first position and the first angle of the probe and the desired imaging plane and based on the layout of the transducer elements.

7. An ultrasound imaging method, comprising:
transmitting ultrasound signals and acquiring three-dimensional volume data of a volume of interest of a subject with an ultrasound probe having a two-dimensional array of transducer elements, wherein the probe is positioned at a first position on the subject and tilted at a first angle relative to the volume of interest and the transducer elements of the probe have a first set of setting parameters, and wherein the three-dimensional volume data of the volume of interest comprises ultrasound echo data of a plurality of scanning planes defined by the first set of setting parameters;
determining a desired imaging plane for the volume of interest in accordance with the three-dimensional volume data;
determining a result whether there is a second set of setting parameters such that the ultrasound signal transmitted from the transducer elements having the second set of setting parameters is able to acquire ultrasound echo data of the desired imaging plane without moving the probe;
deriving—if the result is YES—the second set of setting parameters, and—if the result is NO—deriving a second position, a second angle and a third set of setting parameters such that when the probe is moved to the second position on the subject and tilted at the second angle relative to the volume of interest, the ultrasound signal transmitted from the transducer elements having the third set of setting parameters is able to derive ultrasound echo data of the desired imaging plane; and
adjusting the transducer elements in accordance with the derived second set of setting parameters if the result is Yes, and outputting an instruction to guide a user of the ultrasound imaging system to move the probe so as to be positioned at the second position and tilted at the second angle and adjusting the transducer elements in accordance with the derived third set of setting parameters if the result is NO.

8. The method according to claim 7, further comprising:
displaying an image of the desired imaging plane, which is reconstructed from the ultrasound echo data of the desired imaging plane.

9. The method according to claim 7, wherein
the desired imaging plane for the volume of interest is determined automatically in accordance with the three-dimensional volume data, a clinical objective and a predetermined model.

10. The method according to claim 7, wherein
the desired imaging plane for the volume of interest is determined in accordance with the user's manual selection based on the plurality of images reconstructed from the three-dimensional volume data.

11. The method according to claim 7, wherein
the step of determining a result whether there is a second set of setting parameters such that the ultrasound signal transmitted from the transducer elements having the second set of setting parameters is able to acquire ultrasound echo data of the desired imaging plane without moving the probe is based on the spatial positional relationship between the first position and the first angle of the probe and the desired imaging plane, and is based on the layout of the transducer elements.

* * * * *